(12) United States Patent
Martin

(10) Patent No.: US 6,790,238 B1
(45) Date of Patent: Sep. 14, 2004

(54) ULTRA LOW FRICTION SHEATH FOR PROSTHETICS

(75) Inventor: James Jay Martin, Norman, OK (US)

(73) Assignee: Knit-Rite, Inc., Kansas City, KS (US)

( * ) Notice: Subject to any disclaimer, the term of this patent is extended or adjusted under 35 U.S.C. 154(b) by 33 days.

(21) Appl. No.: 10/205,874

(22) Filed: Jul. 25, 2002

(51) Int. Cl.[7] .................................................. A61F 2/80
(52) U.S. Cl. ............................. 623/36; 602/62; 223/111
(58) Field of Search .......................... 623/33–34, 36–37; 223/111–113; 602/62–63

(56) References Cited

U.S. PATENT DOCUMENTS

| | | | |
|---|---|---|---|
| 4,479,272 A | * 10/1984 | Beldzisky | 623/32 |
| 5,356,057 A | 10/1994 | Vossen | |
| 5,534,034 A | * 7/1996 | Caspers | 623/32 |
| 5,601,220 A | 2/1997 | Vossen | |
| 6,032,839 A | 3/2000 | Joosten et al. | |

FOREIGN PATENT DOCUMENTS

| | | | |
|---|---|---|---|
| EP | 0497858 | 10/1990 | |
| GB | 826041 | * 12/1959 | 623/36 |
| WO | WO 9105498 | 5/1991 | |

OTHER PUBLICATIONS

Easy–Proth Manual: *Dress and Undress Line*, Arion North–America, Inc., 8 pages.

Easy–Proth Manual: *Dress and Undress Line*. Arion North–America, Inc., 1999 (prior to Applicant's effective U.S. filing date of Jul. 25, 2002), 8 pages.

* cited by examiner

*Primary Examiner*—David H. Willse
(74) *Attorney, Agent, or Firm*—Hovey Williams LLP

(57) ABSTRACT

Ultra low friction sheath for facilitating donning and wearing of a prosthesis on a residual limb. The sheath is configured to remain between the residual limb and the prosthesis during normal use of the prosthesis for its intended purpose. A low friction sheath can also be used to help don a shoe on a prosthetic foot.

9 Claims, 2 Drawing Sheets

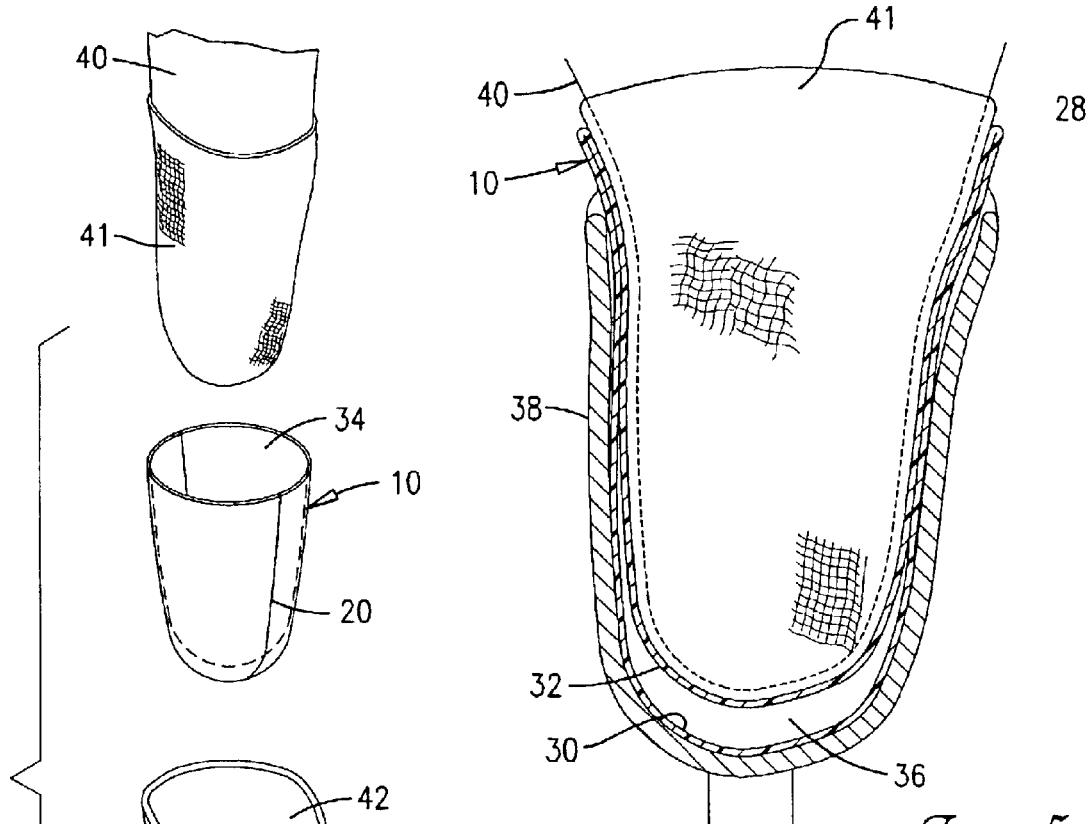
Fig. 5.
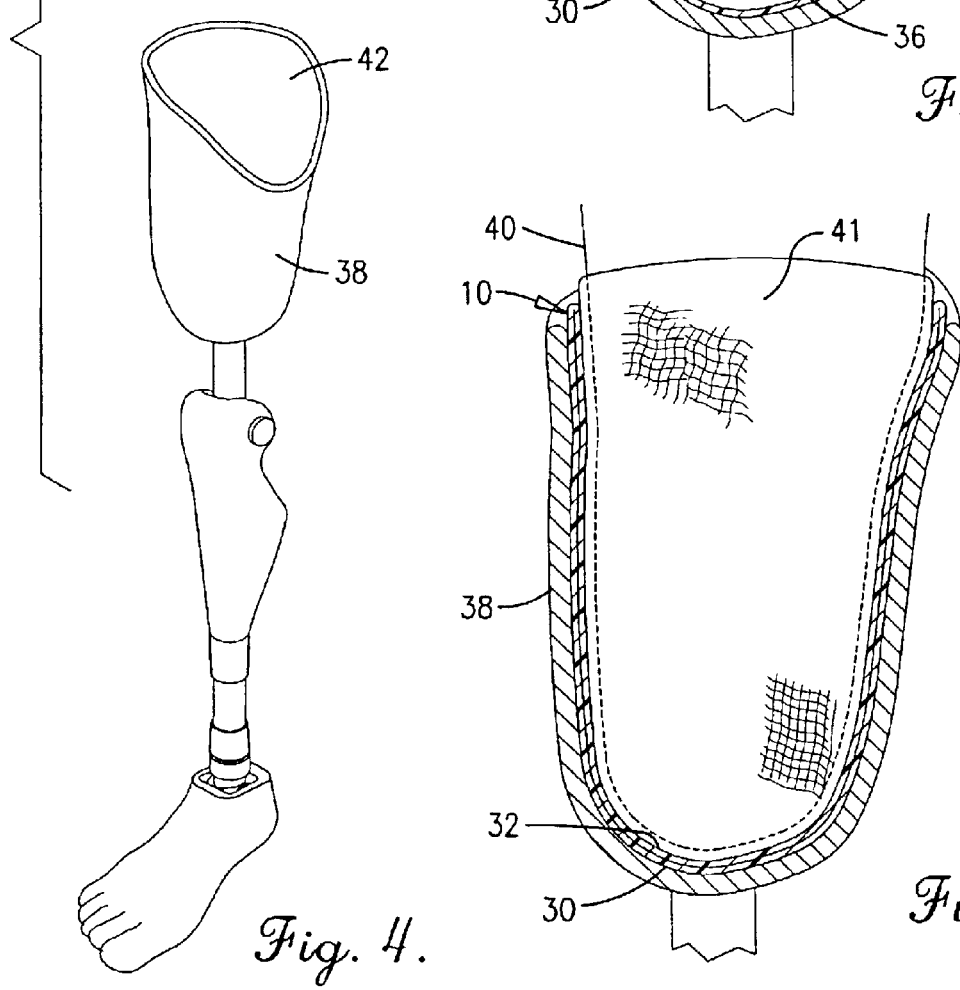
Fig. 4.
Fig. 6.

ULTRA LOW FRICTION SHEATH FOR PROSTHETICS

BACKGROUND OF THE INVENTION

1. Field of the Invention

The present invention relates generally to orthotic and prosthetic devices. In another aspect, the invention concerns a novel sheath system for facilitating the donning and wearing of a prosthesis on a residual limb by reducing the frictional forces between the residual limb and the prosthesis.

2. Description of the Prior Art

Every year, thousands of people undergo amputations. The predominant cause of amputation is peripheral vascular disease (PVD) and/or diabetes. Additional causes of amputation include trauma, congenital abnormalities, and other diseases such as cancer. In many cases amputees are elderly, have poor physical strength, and/or have fragile skin conditions. Thus, physical limitations may inhibit the ability of an amputee to adequately don a prosthesis. Additionally, shear or other forces within the socket of the prosthesis may lead to sores developing on fragile skin.

High frictional and compressional forces between the residual limb of an amputee and the prosthesis may pose many other problems and concerns. Friction within a prosthetic socket interface often increases proximal bunching of prosthetic socks, adductor rolls, proximally directed pressure of soft tissue, and "hammocking" (i.e., lack of distal contact between the residual limb and the prosthesis) due to increased proximal tension from prosthetic sock piles. If these issues are not addressed adequately, the amputee's functional abilities are often limited due to discomfort, fitting limitations, and/or the risk of developing sores on the residual limb. These risks are of great concern for amputees, especially those with conditions that may cause delayed healing, such as PVD or diabetes.

With some traumatic or congenital related amputations, the residual limb itself may present unique fitting considerations due to tissue consistency or irregular bone structure of the residual limb. Thus, the structure of the residual limb itself may cause difficulty in optimally fitting a prosthesis for ease of donning, comfort, and function.

OBJECTS AND SUMMARY OF THE INVENTION

It is an object of the present invention to provide a system for minimizing friction between a prosthesis and a residual limb, thereby facilitating the donning of a prosthesis on a residual limb and the removal of the prosthesis from the residual limb.

A further object of the invention is to provide an ultra low friction sheath having a configuration that allows it to be maintained in the socket of a prosthesis during use of the prosthesis, without causing discomfort to the wearer.

Another object of the invention is to provide a system for reducing proximal bunching of prosthetic socks, adductor rolls, proximally directed pressure of soft tissue, and "hammocking" when a prosthesis is fitted on a residual limb.

Still another object of the invention is to provide a system for facilitating the donning of a prosthesis on a residual limb having an irregular shape or composition.

Yet another object of the invention is to provide a system for facilitating the donning of a shoe on a prosthetic foot.

It should be understood that the above-listed objects are only exemplary, and not all the objects listed above need be accomplished by the invention described and claimed herein.

Accordingly, in one embodiment of the present invention there is provided a low friction sheath for facilitating donning of a prosthesis on a residual limb. The sheath comprises an outer bag and an inner bag substantially received in the outer bag. The outer bag has an outer bag open end and an outer bag closed end, while the inner bag has an inner bag open end and an inner bag closed end. The inner and outer bags are joined to one another at their open ends, and the closed ends of the inner and outer bags have substantially similar rounded shapes.

In another embodiment of the present invention, there is provided a low friction sheath for facilitating donning and wearing of a prosthesis on a residual limb. The sheath comprises a first piece of low friction material, a second piece of low friction material, and a seam joining the first and second pieces of material. The first and second pieces of material have respective first and second rounded proximal ends, rounded distal ends, and circumscribing edges. The seam joins the first and second pieces of material at their circumscribing edges.

In a further embodiment of the present invention, there is provided a low friction sheath for facilitating donning and wearing of a prosthesis on a residual limb. The sheath comprises a hollow body formed primarily of a thin, pliable, low friction material. The body is generally elliptically shaped when in an unfolded position. The body presents first and second spaced-apart ends and a mid portion joining the ends. The body includes a preformed crease extending across the mid portion.

In a still further embodiment of the present invention, there is provided a method of donning a prosthesis on a residual limb and thereafter using the donned prosthesis. The method comprises the steps of: (a) placing a low friction sheath over at least a portion of the residual limb, wherein the sheath is formed primarily of a low friction material having a self coefficient of static friction of less than about 0.4; (b) inserting the sheath and the residual limb at least partly into a socket of a prosthesis; and (c) using the prosthesis for its intended purpose while the sheath is at least partly received in the socket of the prosthesis.

In a yet further embodiment of the present invention, there is provided a method of donning a shoe on a prosthetic foot comprising the steps of: (a) covering at least a portion of the prosthetic foot with a low friction prosthetic sheath; (b) inserting the sheath and the prosthetic foot at least partly into the shoe; and (c) using the shoe and prosthesis for their intended purposes while the sheath is at least partly received in the shoe.

BRIEF DESCRIPTION OF THE DRAWING FIGURES

A preferred embodiment of the present invention is described in detail below with reference to the attached drawing figures, wherein:

FIG. 4 is an isometric assembly view showing the manner in which the sheath can be used to facilitate donning of a prosthesis on a residual limb;

FIG. 5 is a sectional side view of a residual limb being partially inserted into the socket of a prosthesis with the aid of a low friction sheath, particularly illustrating the sheath in its pre-donned position with a gap existing between the inner and outer bags prior to full insertion of the residual limb into the socket;

FIG. 6 is a sectional side view of a residual limb fully inserted into the socket of the prosthesis with the aid of the low friction sheath, particularly illustrating that the gap between the inner and outer bags of the sheath has been eliminated due to low friction sliding of the inner and outer bags on one another;

Figure 7:
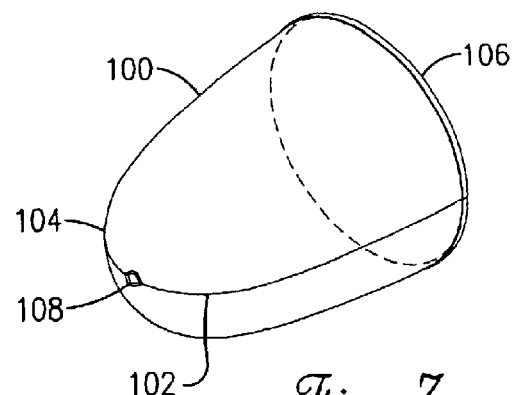
Figure 8:
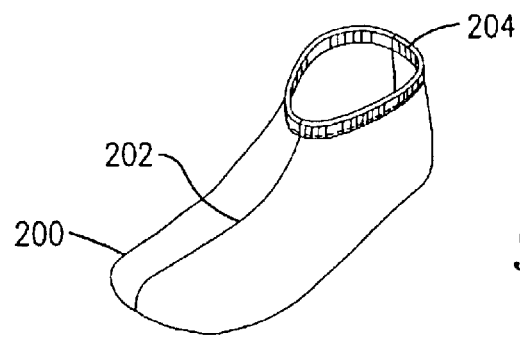

FIG. 7 is an isometric view of a single-layer low friction sheath that can be used to facilitate the donning of a prosthesis on a residual limb, particularly illustrating an opening in the distal end of the sheath through which a mechanical connection between the prosthesis and the residual limb can extend; and FIG. 8 is an isometric view of a single-layer low friction shoe sheath that can be used to facilitate the donning of a shoe on a prosthetic foot.

DETAILED DESCRIPTION OF THE PREFERRED EMBODIMENT

Figure 1:
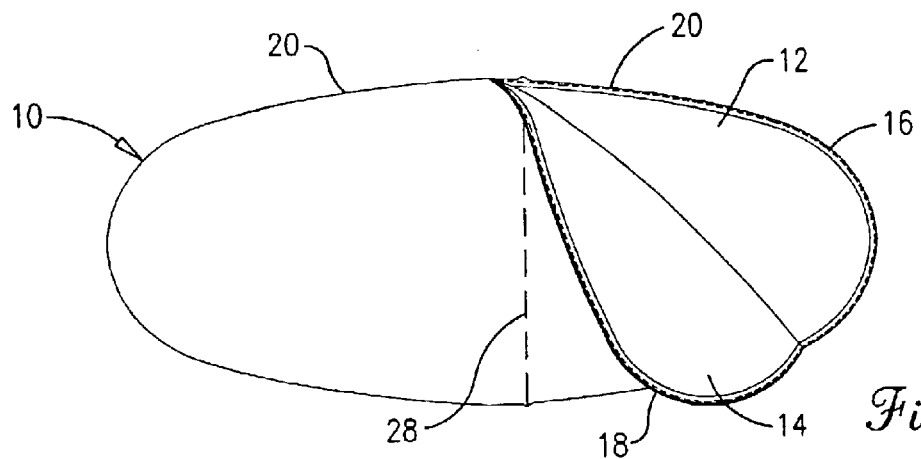
FIG. 1 is a partially disassembled side view of a low friction sheath constructed in accordance with the principles of the present invention, particularly illustrating the construction of the sheath from two similarly shaped, generally elliptical pieces of low friction material joined to one another at their edges by a seam.

Referring initially to FIG. 1, a low friction sheath 10 is illustrated as generally comprising first and second pieces of material 12, 14. First and second pieces of material 12, 14 preferably have substantially the same shape. Most preferably first and second pieces of material 12, 14 are generally elliptical in shape. First and second pieces of material 12, 14 each include first and second circumscribing edges 16, 18. A seam 20 joins first and second pieces of material 12, 14 to one another at circumscribing edges 16, 18.

Figure 2:
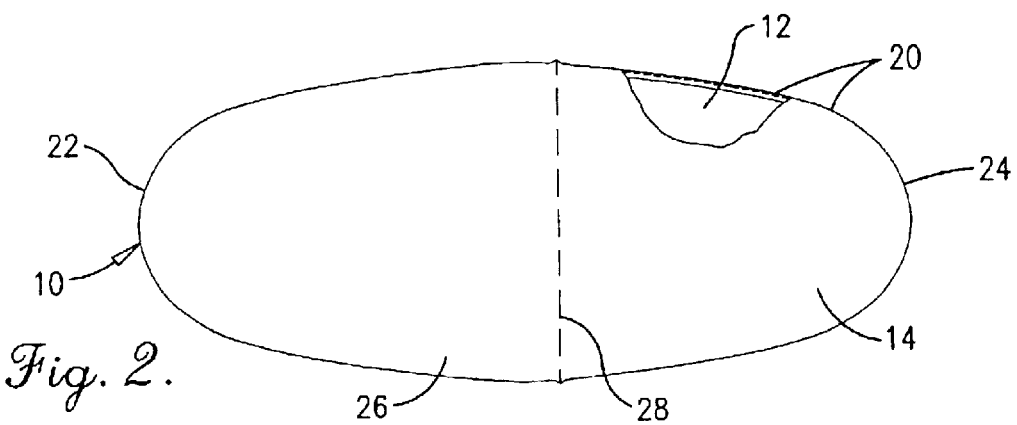
FIG. 2 is a partial cut-away side view of the low friction sheath in an unfolded position, particularly illustrating the continuous seam that circumscribes the sheath, as well as a preformed crease extending across the middle portion of the sheath.

Referring to FIG. 2, low friction sheath 10 is illustrated with seam 20 completely circumscribing sheath 10 with substantially no gaps in seam 20. Sheath 10 generally comprises a first end 22, a second end 24, and a mid portion 26 extending between the first and second ends 22, 24. A preformed crease 28 extends across mid portion 26. Preformed crease 28 can be formed in the fabric by any suitable means known in the art such as, for example, by simply packaging the sheath with the fabric folded in the proper location or by heat pressing the fabric while folded in the proper location.

Figure 3:
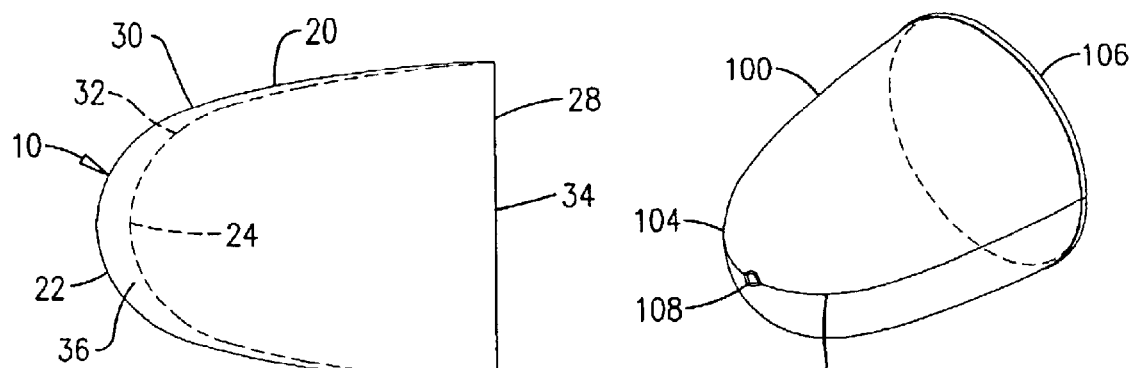
FIG. 3 is a side view of the low friction sheath in a pre-donned position, particularly illustrating the outer and inner bags formed when the sheath is partially folded into itself in the pre-donned position.

Low friction sheath 10 can be shifted from the unfolded position (shown in FIG. 2) to the pre-donned position (shown in FIG. 3) by folding sheath 10 at least partly into itself with second end 24 being shifted towards first end 22. Referring to FIG. 3, when sheath 10 is in the pre-donned position, sheath 10 forms an outer bag 30 and an inner bag 32. Outer bag 30 includes a closed end that is formed of first end 22, while inner bag 32 includes a closed end that is formed of second end 24. Outer and inner bags 30, 32 are joined to one another at a common opening 34. When sheath 10 is in the pre-donned position, preformed crease 28 is positioned proximate common opening 34 and is operable to help maintain sheath 10 in a pre-donned position with the proper gap 36 between first and second ends 22, 24.

Referring to FIG. 4, low friction sheath 10 can be employed to facilitate the donning of a prosthesis 38 on a residual limb 40 by reducing the frictional forces between prosthesis 38 and limb 40 or a prosthetic sock 41 covering limb 40. To don prosthesis 38 on residual limb 40, sheath 10 is placed at least partly over residual limb 40 and prosthetic sock 41 while sheath 10 is maintained in the pre-donned position. Referring now to FIGS. 4 and 5, residual limb 40 and sheath 10 can then be inserted partly into a socket 42 of prosthesis 38 with sheath 10 being substantially maintained in the pre-donned position, so that gap 36 is maintained between outer and inner bags 30, 32. Referring now to FIGS. 4 and 6, residual limb 40 and sheath 10 can then be fully inserted into socket 42 of prosthesis 38, thereby shifting sheath 10 from the pre-donned position to a donned position. Referring to FIGS. 4 through 6, when sheath 10 is shifted from the pre-donned position (shown in FIG. 5) to the donned position (shown in FIG. 6), the outer surface of outer bag 32 slides on the inner surface of outer bag 32 to thereby eliminate gap 36 and facilitate complete insertion of residual limb 40 into socket 42. After complete insertion of residual limb 40 into socket 42, prosthesis 38 can be further secured to residual limb 40 by any attachment means known in the art such as, for example, a suspension belt.

Referring now to FIGS. 1 through 6, in order to facilitate comfort and ease of insertion of residual limb 40 into socket 42, it is preferred for first and second pieces of material 12, 14 to be formed primarily of a thin, pliable, low friction fabric that is substantially devoid of openings. It is preferred for the fabric to have a maximum thickness of less than about 0.025 inches, more preferably less than about 0.015 inches, and most preferably less than 0.01 inches. It is preferred for the fabric to have a weight of less than about 200 denier, more preferably less than about 100 denier, still more preferably less than about 75 denier, even more preferably less than 50 denier, and most preferably in the range of from 20 to 40 denier. Such minimal thickness and weight of the fabric increases the comfort of the wearer by preventing thick bunches of fabric from forming in socket 42 and causing localized pressure on residual limb 40. It is preferred for the fabric to have a self coefficient of static friction of less than about 0.4, more preferably less than about 0.2, still more preferably less than about 0.1, and most preferably less than 0.05. As used herein with reference to a fabric or material, the term "self coefficient of friction" shall denote the coefficient of friction (either static or dynamic) between two layers of the same fabric or material. It is preferred for the fabric to have a self coefficient of dynamic friction of less than about 0.3, more preferably less than about 0.15, still more preferably less than about 0.075, and most preferably less than 0.03. Such a low coefficient of friction substantially enhances the ease of donning prosthesis 38 on residual limb 40 by facilitating the sliding of outer and inner bags 30, 32 on one another when sheath 10 is shifted from the pre-donned position (shown in FIG. 5) to the donned position (shown in FIG. 6). It is preferred for the fabric to be selected from the group consisting of rip-stop nylon, nylon, polyester, polyester-cotton, and combinations thereof. Most preferably, the fabric consists essentially of rip-stop nylon. It is preferred for the fabric to be heat calendered and silicone pretreated in order to reduce its coefficient of friction. Heat calendering is known in the art as a process that involves passing a fabric, under high pressure, between heated rollers to provide a glossiness, hardness, luster, or sheen. Silicone pretreatment is known in the art as a process wherein a fabric is coated with a silicone-containing compound to thereby reduce the coefficient of friction of the fabric or facilitate water repulsion.

The shape of the inventive sheath described herein provides numerous advantages. Prior art sheaths for assisting in the donning of prosthetics on residual limbs typically included loops or tabs on the end of the sheath for allowing the sheath to be removed from the socket of the prosthesis through a hole near the bottom of the socket by grasping the loop or tab and pulling the sheath out of the socket. Such a requirement for removing the sheath from the socket of the prosthesis after donning the prosthesis can be a difficult and time consuming procedure, especially for amputees with limited physical strength and/or dexterity. Further, such prior art devices could not be maintained in the socket of the prosthesis during normal use of the prosthesis due to the discomfort and pressure points caused by the irregularly shaped ends, loops, and/or tabs of the prior art sheaths.

Referring to FIGS. 2, 3, and 6, it is preferred for first and second ends 22, 24 of sheath 10 to have a similar, rounded shape that provides minimal overlapping and bunching of excess material between socket 42 of prosthesis 38 and residual limb 40 when residual limb 40 is received in socket 42. The material, construction, and shape of the inventive sheath 10 allow sheath 10 to remain in socket 42 of prosthesis 38 while residual limb 40 is received in socket 42 and prosthesis 38 is used for its intended purpose. As can be seen in FIGS. 2 and 3, the outer profile of first and second end 22, 24 is substantially smooth and rounded. As used herein with reference to a low friction sheath, the term "smooth outer profile" shall denote an outer surface having substantially no tabs or loops projecting outwardly therefrom. As shown in FIGS. 2 and 3, it is preferred for first and second ends 22, 24 of sheath 10 to have a minimum radius of curvature along seam 20 that minimizes overlap or bunching of excess material when prosthesis 38 is donned on residual limb 40. As used herein with reference to a low friction sheath, the term "minimum radius of curvature" shall denote the minimum radius of curvature of first and second ends 22, 24. Preferably, first and second ends 22, 24 have a minimum radius of curvature of less that about 0.5 inches, more preferably less than about 1 inch, still more preferably less than 2 inches.

Referring to FIG. 7, a single-ply low friction sheath 100 is illustrated as generally comprising a bag formed of two pieces of material joined at their edges by a seam 102. Sheath 100 includes a first end 104 and a second end 106. First end 104 includes a small opening 108 formed by a gap in seam 102. Opening 108 is designed to allow an internal mechanical connection to extend therethrough. The internal mechanical connection can be any conventional mechanical connection known in the art that is operable to releasably couple the lower end of a residual limb and a prosthesis to one another. Single-ply sheath 100 preferably has a similar shape and is made of a similar fabric as the two-ply sheath described above. Although not illustrated in FIGS. 1 through 6, two-ply low friction sheath 10 can also be configured for use with an internal mechanical connection by simply forming openings in first and second ends 22, 24. The openings in ends 22, 24 would be substantially aligned with one another when sheath is in the pre-donned and donned position, thereby allowing the internal mechanical connection to extend therethrough.

Referring to FIG. 8, a single-ply low friction shoe sheath 200 is illustrated as generally comprising a single piece of fabric joined at a seam 202 and an elastic opening 204. Shoe sheath 200 is operable to reduce friction between the foot portion of a prosthesis and a shoe, thereby facilitating insertion and removal of the prosthetic foot into and out of the shoe. To use shoe sheath 200, the amputee first covers the prosthetic foot with sheath 200. The foot and sheath 200 are then inserted into the shoe. The shoe and prosthesis can then be used for their intended purposes while sheath 200 is at least partly received in the shoe. It is preferred for shoe sheath 200 to be formed of the same fabric as sheath 10, describe above with reference to FIGS. 1 through 6.

The preferred forms of the invention described above are to be used as illustration only, and should not be used in a limiting sense to interpret the scope of the present invention. For example, although the invention has been described herein primarily with reference to the donning and wearing of prosthetics and/or orthotics, it should be recognized that the invention finds application in a variety of situations where the donning of a tightly-fitting garment or device can be facilitated by the sliding of two adjacent layers of low friction material on one another. Some alternative uses for the present invention include, for example, aiding in the donning and wearing of wetsuits, biking shorts, and space suits. Obvious modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A method of donning an orthotic or prosthetic device on a human appendage and thereafter using the donned device, said method comprising the steps of:

(a) placing a low friction sheath over at least a portion of the appendage, said sheath being formed primarily of a low friction material having a self coefficient of static friction of less than about 0.4;

(b) inserting the sheath and the appendage at least partly into a socket of the device; and (c) using the device for its intended purpose while the sheath is at least partly received in the socket of the device, said sheath comprising an inner bag and an outer bag each having a respective open and closed end, said inner bar being substantially received in the outer bag, said inner and outer bags being joined to one another at their open ends, step (a) including maintaining a gap between the closed ends of the inner and outer bags, step (b) including substantially eliminating the gap between the closed ends of the inner and outer bags.

2. A method according to claim 1, said sheath comprising two adjacent layers of the low friction material, werein one layer comprises the inner bag and the other layer comprises the outer bag, said adjacent layers of the low friction material having a static coefficient of friction there between of less than about 0.2.

3. A method according to claim 2, step (b) including sliding the adjacent layers on one another.

4. A method according to claim 3; and (d) subsequent to step (c), removing the sheath and the appendage from the socket, step (d) including sliding the adjacent layers on one another.

5. A method according to claim 3,
said static coefficient of friction between the adjacent layers of the low friction material being less than about 0.1,
said adjacent layers of the low friction material having a dynamic coefficient of friction there between of less than about 0.075.

6. A method according to claim 1, said closed ends of the inner and outer bags having substantially the same shape, said closed ends of the inner and outer bags being generally rounded.

7. A method according to claim 1,
said low friction material having a weight of less than about 100 denier.

8. A method according to claim 7,
said low friction material comprising rip-stop nylon.

9. A method according to claim 8,
said rip-stop nylon being heat calendered and silicone pretreated.

\* \* \* \* \*